United States Patent [19]

Spickett et al.

[11] 4,447,417

[45] May 8, 1984

[54] BASIC ALUMINIUM MAGNESIUM CARBONATE

[75] Inventors: Robert G. W. Spickett; Jacinto M. Mauri; Jesus E. B. Puchades, all of Barcelona, Spain

[73] Assignee: Anphar S.A., Madrid, Spain

[21] Appl. No.: 12,435

[22] Filed: Feb. 15, 1979

[30] Foreign Application Priority Data

Feb. 17, 1978 [GB] United Kingdom ................ 6416/78

[51] Int. Cl.$^3$ .............................................. A61K 33/10
[52] U.S. Cl. ..................................... 424/156; 423/430
[58] Field of Search .......................... 424/156; 423/430

[56] References Cited

U.S. PATENT DOCUMENTS 2,958,626  11/1960  Schenck et al. .................... 424/156
3,272,703   9/1966  Rubino et al. ...................... 424/156

FOREIGN PATENT DOCUMENTS 1059495  2/1967  United Kingdom ................ 424/156
1184332  3/1970  United Kingdom ................ 424/156
1185920  3/1970  United Kingdom ................ 424/156
1348702  3/1974  United Kingdom ................ 424/156

*Primary Examiner*—Frederick E. Waddell
*Attorney, Agent, or Firm*—Morgan, Finnegan, Pine, Foley & Lee

[57] ABSTRACT

A new basic aluminium magnesium carbonate of the formula $Al_2Mg_6(OH)_{14}(CO_3)_2.4H_2O$ has been found to be useful in pharmaceutical formulations for the treatment of upper gastrointestinal tract disturbances associated with excess acid and pepsin secretion or biliary reflux.

5 Claims, No Drawings

BASIC ALUMINIUM MAGNESIUM CARBONATE

THIS INVENTION relates to a new therapeutically useful crystalline basic aluminium magnesium carbonate of the formula:

$$Al_2Mg_6(OH)_{14}(CO_3)_2 \cdot 4H_2O \qquad \text{I},$$

to a process for its preparation and pharmaceutical compositions containing it.

Aluminium hydroxide gels and mixtures of these with magnesium hydroxide have been extensively used in pharmaceutical formulations as antacids for the treatment of gastrointestinal disturbances associated with the presence of excess acid in the stomach. A disadvantage of such formulations is that excessive alkalinization occurs with consequent acid rebound. Furthermore, as current medical opinion has clearly accepted the importance of refluxed bile acids in many disorders of the upper gastrointestinal tract, the inability of these preparations to inactivate bile acids further limits their efficacy. In addition, aluminium hydroxide gels on ageing undergo structural changes to give products with reduced acid neutralizing properties. The new compound I does not suffer from these disadvantages and may be used to give stable pharmaceutical formulations for the treatment of upper gastrointestinal tract disturbances associated with excess acid and pepsin secretion or biliary reflux, such as oesophagitis, peptic ulcer, hyperacidity, heart burn, dyspepsia and hiatus hernia, as the compound has improved acid neutralizing and binding properties, inactivates pepsin even at low pH, and binds bile acids to a greater extent than aluminium hydroxide gels.

According to a feature of the invention, the compound of formula I is prepared by a process which comprises heating a mixture of aluminum hydroxide and magnesium hydroxide in the appropriate molecular proportions (viz. 6 moles of magnesium hydroxide per mole of $Al_2O_3$ present) in the presence of carbon dioxide in an aqueous medium containing ammonia or a water-soluble organic nitrogen-containing base at a temperature between 70° and 100° C. at atmospheric pressure, and separating from the reaction mixture an aluminium magnesium carbonate of formula I. The amount of ammonia or water-soluble organic base used is critical and quantities greater than 6 moles per mole of $Al_2O_3$ present in the reaction mixture are necessary to ensure complete reaction. The progress of the reaction may be judged by the transformation of the crystalline starting materials to a gel. On completion of the reaction, the product is collected by filtration, washed with water and dried to give the product I.

The carbon dioxide necessary for the formation of the new basic salt is suitably supplied by passing a stream of the gas through the reaction mixture for a period of time and at a sufficient rate to produce the salt of formula I, for example from 1 to 12 (preferably 6 to 8) hours at the reflux temperature of the reaction mixture.

Suitable water-soluble organic nitrogen-containing bases for inclusion in the reaction mixture are mono-, di- and tri-alkylamines containing up to 4 carbon atoms in the alkyl radical(s), such as methyl, ethyl, propyl or butylamines, pyridine or piperidine, and more particularly triethylamine.

By a similar procedure the synthesis of a naturally occuring mineral, hydrotalcite of formula:

$$Al_2Mg_6(OH)_{16}CO_3 \cdot 4H_2O \qquad \text{II}$$

has been described by Kobo et al., Arch. Pract. Pharm. 29 (3), 215–219, 1969, and in French Brevet d'Invention No. 1532167. Confirmation that the structure of I is different from that of II has been obtained by elemental analysis, acid neutralization curves, infrared and X-ray spectra and by differential thermal analysis. Thus, the carbon dioxide content varies between 13.7 and 14.2% for compound I, which is substantially in accordance with the theoretical value of 13.97%. The carbon dioxide content of natural and synthetic hydrotalcite varies between 7.3 and 7.7%. The infrared spectrum of hydrotalcite shows an intense band at 1380 cm$^{-1}$ and a shoulder between 1610 and 1480 cm$^{-1}$ while in the infrared spectrum of compound I the band at 1480 cm$^{-1}$ has increased in intensity so that is comparable to that at 1380 cm$^{-1}$ and another equally intense band appears at 1420 cm$^{-1}$. The rest of the spectrum—as would be expected—is very similar.

On differential thermal analysis two endotherms at temperatures 500° K. and 700° K. have been observed for hydrotalcite and compound I, but the ratio of the areas is higher for compound I than for hydrotalcite which coincides with the higher content of carbon dioxide of the former.

The X-ray diffraction spectra (see following Table 1) show that, apart from a slight difference in the lines at about 7.69 Å, the spectra of natural and synthetic hydrotalcite are identical (Kobo et al., loc cit). All the intense lines from 1.49 Å to 2.56 Å appear in all three spectra, but in compound I these lines are more intense than the corresponding lines in natural and synthetic hydrotalcite. In the X-ray diffraction spectrum of compound I four lines 2.893, 3.817, 5.752 and 7.595 are present, which do not appear in the spectrum of natural and synthetic hydrotalcite. Only two intense lines 3.88 and 7.69 (7.75) are observed above 2.6 Å in the spectra of the latter compounds.

TABLE 1

| X-Ray diffraction spectra (intense lines only) | | |
|---|---|---|
| Compound I d Å | Hydrotalcite ASTM CARD d Å | Synthetic hydrotalcite Kobo et al (loc cit) d Å |
| — | — | 7.75 |
| — | 7.69 | — |
| 7.595 | — | — |
| 5.752 | — | — |
| — | 3.88 | 3.89 |
| 3.817 | — | — |
| 2.893 | — | — |
| 2.563 | 2.58 | 2.59 |
| 2.291 | 2.30 | 2.30 |
| 1.941 | 1.96 | 1.96 |
| 1.525 | 1.53 | 1.53 |
| 1.496 | 1.50 | 1.50 |

In vitro studies of antacid activity (velocity of reaction, duration of activity, total acid consumption at different pH's, total neutralization capacity and antacid activity against simulated gastric acid juice) and anti-pepsin activity as well as studies of the absorption of bile acids have shown that compound I has advantages over preparations which contain aluminium hydroxide gels, mixtures of aluminium and magnesium hydroxide gels, and aluminium magnesium trisilicate. It is also superior to a mixture of the components used for its preparation and to hydrotalcite.

To measure the antacid activity in simulated gastric juice the technique of Holbert et al. (J. Amer. Pharm. Assoc. 37, 292, 1948) was employed, appropriately modified so that an automatic titrator could be used. Approximately 0.125 g of powder was added to 20 ml of simulated gastric juice (U.S.P.) and stirred vigorously at 37° C. The pH was registered at 1, 5 and 10 minutes and then the automatic burette was started and synthetic gastric juice was added at a rate of 0.7 ml/min. until the pH fell below 3. The time taken and the amount of gastric juice added to reach pH 3 was observed. Of the three types of gastric juice used, one did not contain pepsin, one contained the amount specified in the U.S.P. and the third contained double the amount of pepsin normally present.

The results are shown in Table 2.

TABLE 2

| Antacid | Type of gastric juice*** | pH of suspension after 1 min. | Vol. of gastric juice added ml. |
|---|---|---|---|
| $F_1$* | SP | 3.30 | 17.43 |
| | N | 2.93 | 7.40 |
| | DP | 2.79 | 4.80 |
| $F_2$* | SP | 1.40 | 1.92 |
| | N | 1.95 | 1.70 |
| | DP | 2.65 | 2.40 |
| Hydrotalcite | SP | 3.52 | 13.5 |
| | N | 3.42 | 13.55 |
| | DP | 3.16 | 12.20 |
| Compound of formula I | SP | 4.00 | 10.9 |
| | N | 4.25 | 21.2 |
| | DP | 4.55 | 22.36 |
| Stoichiometric mixture** | SP | 4.64 | 7.96 |
| | N | 4.62 | 10.50 |
| | DP | 4.25 | 12.40 |

*$F_1$, dry aluminium hydroxide gel U.S.P., $F_2$ mixed aluminium-magnesium hydroxide gel, Magaldrate U.S.P.
**Stoichiometric mixture of aluminium hydroxide and magnesium hydroxide used for the preparation of compound I.
***SP, without pepsin; N, normal U.S.P. simulated gastric juice; DP, with double quantity of pepsin.

From all the parameters measured it is clear that compound I is superior to the other products investigated. Like hydrotalcite, it was a high velocity of neutralisation (the pH after 1 minute being in the zone considered to be optimal, i.e. pH 3–5). Unlike the other substances, compound I also showed an increased ability to absorb acid in the presence of pepsin, and in U.S.P. simulated gastric juice had the highest buffering capacity.

Comparison of the acid neutralisation curves of suspensions of the products in water using an automatic titrator with pH stat set at 2, 3 and 4, further differentiates compound I from the other substances. Its acid-binding capacity was higher at pH 4 than any of the other substances, which confirms the results of the above experiment that compound I can maintain its neutralizing activity in spite of continued secretion of hydrochloric acid for a longer period of time than hydrotalcite.

The ability of compound I to absorb bile acids was measured at pH 7 and pH 4 (the analytical method was based on the reaction between sulphuric acid, furfural and cholic acid; Pettenkofer, Ann. Chem. Pharm. 52, 90, 1884). The product was suspended in the appropriate buffer and a solution of the bile acid or ox bile was added, samples being taken at intervals of time. The percentage of bile acid absorbed at these time intervals was measured and is shown in Table 3.

TABLE 3

Percentage absorption of bile acids by compound I

| Bile Acid | Buffer pH 4 | | Buffer pH 7 | |
|---|---|---|---|---|
| | 1 hr | 3 hr | 1 hr | 3 hr |
| Cholic Acid | 80.5 | 86.3 | 0 | 12 |
| Taurochloic acid | 65.4 | 71.7 | 0.6 | 20.8 |
| Ox bile | 69.0 | 70.0 | 17.3 | 25.8 |

It can be seen from Table 3 that compound I has a high capacity for absorbing bile acids at pH 4, but at pH 7 this capacity is considerably reduced. Thus, when biliary reflux into the stomach occurs, where a pH in the region of 4 would be expected, compound I will absorb these acids, thereby limiting their aggressive effect on the stomach wall. However, in the intestine (pH 6–8) these acids will be free to carry out their normal physiological function.

This ability of compound I to neutralize hydrochloric acid and to inactivate pepsin and bile acids has been amply confirmed in vivo using a variety of experimental subjects. In rats with 4 hour pyloric ligatures of the stomach compound I (31.25–500 mg/kg orally) administered 1 hour before sacrifice caused dose dependent increases in the pH of the stomach contents and reduced the total acid content by up to 85%. Under the same conditions aluminium hydroxide had much less influence on pH and was virtually without effect on total acid content (12% reduction). When compound I (31.25 mg/kg orally) was administered at the same time as the operation and the ligature left in place for 18 hours, there was a 58% reduction in the incidence of ulcers compared with placebo treated controls. Under the same conditions 125 mg/kg of aluminium hydroxide was required to obtain a 43% reduction in ulceration. Gastric juice from the 4 hour ligature experiments was also tested for pepsin activity. At the higher doses enzyme activity was reduced by 78.9% which was only partly due to the raised pH, as when the pH of the gastric juice was readjusted to 2 (optimal for pepsin activity) enzyme activity was still significantly reduced (32.5%). Under identical experimental conditions aluminium hydroxide was without effect on the pepsin activity of the gastric juice. In a further series of experiments the detergent action of bile was used to sensitize the rat stomach to the ulcerogenic action of indomethacin. Under these conditions compound I (31.25–125 mg/kg orally) statistically reduced the incidence of ulcers by up to 54%. Under the same conditions aluminium hydroxide produced a non-significant 32% inhibition.

Compound I also demonstrated superior antacid and antipepsin properties in relation to aluminium hydroxide gel in human volunteers. Gastric acid secretion was induced by injection of pentagastrin (6 $\mu$g/kg i.m.). Thirty minutes later a suspension of 1 g of compound I or aluminium hydroxide was given (2 groups of 6 volunteers, double blind parallel). Samples of gastric juice were taken before giving pentagastrin (basal level), 30 minutes after injection of pentagastrin and at intervals of 30, 60, 90 and 120 minutes after giving the antacids. In each case the pH, free acid content and pepsin content were measured. It was shown that compound I reduced the free hydrochloric acid levels more rapidly and had a longer duration of action than aluminium hydroxide gel and that it also has a greater antipepsin effect.

Useful therapeutic doses of compound I are between 0.5 and 10 g daily.

Also included within the scope of the present invention are pharmaceutical compositions which comprise as active ingredient compound I in association with a pharmaceutically-acceptable carrier or diluent. The compositions are made in a form suitable for oral administration which may take the form of tablets, capsules, suspensions or powders and such preparations may be made by methods well known in the art.

In another aspect of the invention, compound I may be mixed with other agents with a specific effect on gastrointestinal disturbances such as spasmolytic or anti-ulcer agents, regulators of gastrointestinal motility, minor or major tranquillizers and gas dispersing agents.

The following Examples illustrate the preparation of the compound of the present invention.

EXAMPLE 1

A suspension of aluminium hydroxide (9.57 g, corresponding to 5.09 g of $Al_2O_3$; 0.05 moles), magnesium hydroxide of 92.09% purity (18.87 g; 0.3 moles), concentrated ammonium hydroxide (4.89 ml; 0.33 moles) and water (500 ml) was boiled under reflux for 6 hours while a stream of carbon dioxide was passed through the mixture. Then the reaction mixture was cooled, and the insoluble compound was filtered off, washed several times with water and dried in vacuo at a temperature of 60° C. Basic aluminium magnesium carbonate of formula I (31.1 g) was obtained.

Analysis: Calculated for $Al_2Mg_6(OH)_{14}(CO_3)_2.4H_2O$; $Al_2O_3$: 16.18%, $MgO$: 38.39%, $CO_2$: 13.97%; $H_2O$: 31.46. Found: $Al_2O_3$: 16.52%, $MgO$: 38.03%, $CO_2$: 13.76%, $H_2O$: 31.87.

Infrared spectrum: three intense bands at 1480, 1420 and 1380 $cm^{-1}$.

EXAMPLE 2

A suspension of aluminium hydroxide (9.57 g, corresponding to 5.09 g of $Al_2O_3$; 0.05 moles) magnesium hydroxide of 92.09% purity (18.87 g; 0.3 moles), triethylamine (33.4 g; 0.33 moles) and water (500 ml) was boiled under reflux for 8 hours while a stream of carbon dioxide was passed through the mixture. After cooling, the insoluble compound was filtered off, washed several times with water and dried at 60° C. under reduced pressure. Basic aluminium magnesium carbonate of formula I (30.8 g) was obtained. The analytical results of the product were the same as those mentioned in Example 1.

The following Examples illustrate pharmaceutical compositions according to the present invention.

EXAMPLE 3

10,000 Units of suspension, each unit containing 500 mg of basic aluminium magnesium carbonate of formula I per 5 ml of suspension, were prepared from the following formulation:

| | |
|---|---|
| basic aluminium magnesium carbonate of formula I | 5000 g |
| sorbitol, 70% aqueous solution | 5000 g |
| sodium carboxymethylcellulose, 400 cp/2% | 650 g |
| methyl p-hydroxybenzoate sodium salt | 112.5 g |
| propyl p-hydroxybenzoate sodium salt | 12.5 g |
| saccharin sodium salt | 50 g |
| anethol | 20 g |
| water q.s. | 50 liters. |

Procedure:

The sodium carboxymethylcellulose, sodium ethyl hydroxybenzoate, sodium propyl hydroxybenzoate and saccharin sodium salt were dissolved in 35 liters of demineralized water with stirring. The sorbitol solution was added, and the basic aluminium magnesium carbonate was dispersed in the solution. Then the anethol was added and the volume was made up to 50 liters with water. The resulting suspension was passed through a colloidal mill and afterwards inserted into unidose aluminium coated polyethylene sachets so that each contained 5 ml of suspension.

EXAMPLE 4

10,000 Tablets each containing 500 mg of basic aluminium magnesium carbonate of formula I were prepared from the following formulation:

| | |
|---|---|
| basic aluminium magnesium carbonate of formula I | 5000 g |
| mannitol | 6000 g |
| corn starch | 195 g |
| soluble starch | 325 g |
| saccharin sodium salt | 20 g |
| mint flavour (dry powder) | 10 g |
| magnesium stearate | 100 g. |

Procedure:

The basic aluminium magnesium carbonate and the mannitol were mixed and granulated with a solution of the saccharin sodium salt and the soluble starch in 6 liters of water. The granulate was dried and then passed through a screen with an opening of 0.5 mm. This granulate was then mixed with the rest of the compounds and the mixture compressed into 1.165 g tablets using a 15 mm disc and flat bevel edged punches.

EXAMPLE 5

5,000 Units of powder, each containing 500 mg of basic aluminium magnesium carbonate of formula I per 3 g of powder, were prepared from the following formulation:

| | |
|---|---|
| basic aluminium magnesium carbonate of formula I | 2500 g |
| mannitol | 12175 g |
| colloidal silicon dioxide | 150 g |
| saccharin sodium salt | 50 g |
| mint flavour (dry powder) | 125 g |

Procedure:

The basic aluminium magnesium carbonate was micronized in a jet-mill and then mixed with the rest of the components. The resulting powder was placed in unidose sachets so that each contained 3 g.

We claim:

1. A basic crystalline aluminium magnesium carbonate of the formula $Al_2Mg_6(OH)_{14}(CO_3)_2.4H_2O$.

2. A pharmaceutical antacid composition which comprises an effective amount of a basic crystalline aluminium magnesium carbonate of the formula $Al_2Mg_6(OH)_{14}(CO_3)_2.4H_2O$ in association with a pharmaceutically-acceptable carrier or diluent.

3. A pharmaceutical composition according to claim 2 in a form suitable for oral administration.

4. A method for the treatment of upper gastrointestinal tract disturbances in a patient associated with excess acid and pepsin secretion or biliary reflux which comprises administering orally to the patient an effective amount of a basic crystalline aluminium magnesium carbonate of the formula $Al_2Mg_6(OH)_{14}(CO_3)_2.4H_2O$.

5. A method according to claim 4 in which the amount of said basic aluminium magnesium carbonate administered orally to the patient is from 0.5 through 10 g per day.

* * * * *